United States Patent [19]

Lesher et al.

[11] 4,313,951

[45] Feb. 2, 1982

[54] 3-SUBSTITUTED-6-(LOWER-ALKYL)-5-(PYRIDINYL)-2(1H)-PYRIDINONES, THEIR CARDIOTONIC USE AND INTERMEDIATES THEREFOR

[75] Inventors: George Y. Lesher; Richard E. Philion, both of Schodack, N.Y.

[73] Assignee: Sterling Drug Inc., New York, N.Y.

[21] Appl. No.: 198,461

[22] Filed: Oct. 20, 1980

Related U.S. Application Data

[63] Continuation-in-part of Ser. No. 97,504, Nov. 26, 1979, abandoned.

[51] Int. Cl.$^3$ .................... C07D 401/04; A61K 31/44
[52] U.S. Cl. .................... 424/263; 546/257; 546/258
[58] Field of Search ................. 424/263; 546/257, 258

[56] References Cited

U.S. PATENT DOCUMENTS

| | | | |
|---|---|---|---|
| 4,004,012 | 1/1977 | Lesher et al. | 546/257 |
| 4,072,746 | 2/1978 | Lesher et al. | 546/257 |
| 4,107,315 | 8/1978 | Lesher et al. | 424/263 |
| 4,137,233 | 9/1979 | Lesher et al. | 546/257 |

*Primary Examiner*—John M. Ford
*Attorney, Agent, or Firm*—Robert K. Bair; B. Woodrow Wyatt

[57] ABSTRACT

$1-R_1$-3-[amino, cyano, carbamyl, halo, lower-alkylamino, di-(lower-alkyl)amino or lower-acylamino]-6-(lower-alkyl)-5-(pyridinyl)-2(1H)-pyridinones or pharmaceutically-acceptable acid-addition or cationic salts thereof are useful as cardiotonic agents, where $R_1$ is hydrogen, lower-alkyl or lower-hydroxyalkyl. $1-R_1$-3-amino-6-(lower-alkyl)-5-(pyridinyl)-2(1H)-pyridinones are prepared by hydrolyzing the corresponding 3-cyano compounds to produce the corresponding 3-carbamyl compounds and reacting the latter with a reagent capable of converting carbamyl to amino. The $1-R_1$-3-cyano-6-(lower-alkyl)-5-(pyridinyl)-2(1H)-pyridinones are prepared by reacting (pyridinylmethyl) lower-alkyl ketones with dimethylformamide di-(lower-alkyl) acetal to produce 1-(pyridinyl)-2-(dimethylamino)ethenyl lower-alkyl ketone and reacting said ketones with N-$R_1$-α-cyanoacetamide to produce the $1-R_1$-3-cyano-6-(lower-alkyl)-5-(pyridinyl)-2(1H)-pyridinones. Also shown are the conversions: of the 3-cyano compounds to the 3-H compounds; of the 3-H compounds to the 3-halo compounds; of the 3-halo compounds to the 3-[mono-(lower-alkyl)- or di-(lower-alkyl)-amino]compounds; and, of the 3-amino compounds to the 3-lower-acylamino or 3-[mono-(lower-alkyl)- or di-(lower-alkyl)amino] compounds.

26 Claims, No Drawings

3-SUBSTITUTED-6-(LOWER-ALKYL)-5-(PYRIDINYL)-2(1H)-PYRIDINONES, THEIR CARDIOTONIC USE AND INTERMEDIATES THEREFOR

CROSS-REFERENCE TO RELATED APPLICATION

This application is a continuation-in-part of copending application Ser. No. 97,504, filed Nov. 26, 1979 and now abandoned.

The 5-(pyridinyl)-6-(lower-alkyl)-2(1H)-pyridinones which are disclosed herein as intermediates for the preparation of the corresponding 3-halo compounds are disclosed as cardiotonics and are claimed in copending application Ser. No. 204,726, filed Nov. 6, 1980, a continuation-in-part of copending application Ser. No. 135,100, filed Mar. 28, 1980. Said 5-(pyridinyl)-6-(lower-alkyl)-2(1H)-pyridinones are also disclosed as intermediates for preparing 2-halo-5-(pyridinyl)-6-(lower-alkyl)pyridines in copending applications Ser. Nos. 135,100, 135,105 and 135,211, all filed Mar. 28, 1980.

BACKGROUND OF THE INVENTION (a) Field of the Invention

This invention relates to 3-substituted-6-(lower-alkyl)-5-(pyridinyl)-2(1H)-pyridinones, their use as cardiotonic agents, and their preparation.

(b) Description of the Prior Art

Lesher and Opalka [U.S. Pat. Nos. 4,004,012, issued Jan. 18, 1977, and 4,072,746, issued Feb. 7, 1978] show as cardiotonic agents 3-amino(or cyano)-5-(pyridinyl)-2(1H)-pyridinones and as intermediates, the corresponding 3-carbamyl compounds, alternately named 1,2-dihydro-2-oxo-5-(pyridinyl)nicotinamides, which are converted to the corresponding 3-amino compounds by reaction with a reagent capable of converting carbamyl to amino, e.g., by heating with an alkali metal hypohalite. A preferred embodiment of these compounds is 3-amino-5-(4-pyridinyl)-2(1H)-pyridinone, now generically known as amrinone and alternatively named 5-amino-[3,4'-bipyridin]-6(1H)-one. One method shown for preparing the 3-cyano-5-(pyridinyl)-2(1H)-pyridinones, alternatively named 1,2-dihydro-2-oxo-5-(pyridinyl)nicotinonitriles, is the reaction of $\alpha$-(pyridinyl)-$\beta$-(dialkylamino)acrolein with $\alpha$-cyanoacetamide. U.S. Pat. No. 4,072,746 also shows 3-Q-5-(pyridinyl)-2(1H)-pyridinones where Q is hydrogen, halo, lower-alkylamino, di-(lower-alkyl)amino and NHAc where Ac is lower-alkanoyl or lower-carbalkoxy. The disclosure of U.S. Pat. No. 4,072,746 also is shown in Lesher and Opalka U.S. Pat. Nos. 4,107,315, 4,137,233, 4,199,586 and 4,225,715.

SUMMARY OF THE INVENTION

In a composition of matter aspect, the invention relates to 1-$R_1$-3-Q-5-PY-6-(lower-alkyl)-2(1H)-pyridinones, which are useful as cardiotonic agents, where Q, $R_1$ and PY are defined hereinbelow. Some of these compounds, e.g., those where Q is cyano, carbamyl, halo, are also useful as intermediates in preparing corresponding said compounds where Q is amino, lower-alkylamino, di-(lower-alkyl)amino, hydrogen and lower-acylamino.

The invention in a process aspect resides in process of producing 1-$R_1$-3-amino-5-PY-6-(lower-alkyl)-2(1H)-pyridinone which comprises hydrolyzing 1-$R_1$-3-cyano-5-PY-6-(lower-alkyl)-2(1H)-pyridinone to produce the corresponding 3-carbamyl compound and reacting the latter with a reagent capable of converting carbamyl to amino.

In another process aspect the invention comprises reacting PY-methyl lower-alkyl ketone with dimethylformamide di-(lower-alkyl) acetal to produce 1-PY-2-(dimethylamino)ethenyl lower-alkyl ketone and reacting the latter with N-$R_1$-$\alpha$-cyanoacetamide to produce 1-$R_1$-3-cyano-5-PY-6-(lower-alkyl)-2(1H)-pyridinone.

Another composition of matter aspect of the invention relates to 1-(pyridinyl)-2-(dimethylamino)ethenyl lower-alkyl ketones or pharmaceutically-acceptable acid-addition salt thereof, useful as intermediates in preparing 1-$R_1$-3-cyano-5-PY-6-(lower-alkyl)-2(1H)-pyridinones.

In another process aspect the invention comprises reacting 1-$R_1$-5-PY-6-(lower-alkyl)-2(1H)-pyridinone with halogen, preferably bromine or chlorine, to produce 1-$R_1$-3-halo-5-PY-6-(lower-alkyl)-2(1H)-pyridinone and reacting said 3-halo compound with a lower-alkylamine or di-(lower-alkyl)amine to produce the corresponding 1-$R_1$-3-(lower-alkylamino)-5-PY-6-(lower-alkyl)-2(1H)-pyridinone or 1-$R_1$-3-[di-(lower-alkyl)amino]-5-PY-6-(lower-alkyl)-2(1H)-pyridinone.

An alternative process aspect of the invention for preparing 1-$R_1$-3-[mono- or di-(lower-alkyl)amino]-5-PY-6-(lower-alkyl)-2(1H)-pyridinone comprises reacting the corresponding 3-amino compound with one or two molar equivalents of a lower-alkylating agent. A preferred embodiment of this alternative process comprises reacting 1-$R_1$-3-amino-5-PY-6-(lower-alkyl)-2(1H)-pyridinone with a methylating mixture of formic acid and formaldehyde to produce 1-$R_1$-3-dimethylamino-5-PY-6-(lower-alkyl)-2(1H)-pyridinone.

In another process aspect the invention comprises reacting 1-$R_1$-3-amino-5-PY-6-(lower-alkyl)-2(1H)-pyridinone with a lower-acylating agent to produce 1-$R_1$-3-acylamino-5-PY-6-(lower-alkyl)-2(1H)-pyridinone.

A composition aspect of the invention relates to a cardiotonic composition for increasing cardiac contractility in a patient, said composition comprising a pharmaceutically-acceptable carrier and, as the active ingredient thereof, an effective amount of a cardiotonic 1-$R_1$-3-substituted-5-PY-6-(lower-alkyl)-2(1H)-pyridinone.

In a method aspect, the invention relates to a method for increasing cardiac contractility in a patient requiring such treatment which comprises the administration of a medicament comprising a pharmaceutically-acceptable carrier and, as the active component thereof, an effective amount of a cardiotonic 1-$R_1$-3-substituted-5-PY-6-(lower-alkyl)-2(1H)-pyridinone.

DETAILED DESCRIPTION INCLUSIVE OF PREFERRED EMBODIMENTS

In a composition aspect the invention resides in the compounds having formula I

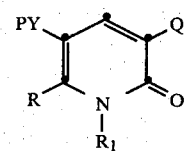

where Q is amino, cyano, carbamyl, halo, lower-alkylamino, di-(lower-alkyl)amino or lower-acylamino, $R_1$ is hydrogen, lower-alkyl or lower-hydroxyalkyl, R is lower-alkyl and PY is 4- or 3- or 2-pyridinyl or 4- or 3- or 2- pyridinyl having one or two lower-alkyl substituents, or pharmaceutically-acceptable acid-addition or cationic salt thereof. The compounds of formula I are useful as cardiotonic agents, as determined by standard pharmacological evaluation procedures. The compounds of formula I where Q is carbamyl and cyano also are useful as intermediates for preparing the corresponding compounds where Q is amino. The compounds of formula I where Q is halo also are useful as intermediates for preparing the corresponding 3-[mono- or di-(lower-alkyl)amino] compounds. Preferred embodiments are those of formula I where Q is amino or cyano, PY is 4-pyridinyl or 3-pyridinyl and R is methyl or ethyl. Particularly preferred embodiments are 1,2-dihydro-6-methyl-2-oxo-5-(4-pyridinyl)nicotinonitrile (I where Q is CN, $R_1$ is H, PY is 4-pyridinyl and R is methyl), 3-amino-6-ethyl-5-(4-pyridinyl)-2(1H)-pyridinone (I where Q is $NH_2$, $R_1$ is H, PY is 4-pyridinyl and R is ethyl), and 3-amino-5-(4-pyridinyl)-6-methyl-2(1H)-pyridinone (I where Q is $NH_2$ $R_1$ is H, PY is 4-pyridinyl and R is methyl), or pharmaceutically-acceptable acid-addition salt thereof. These particularly preferred embodiments were found to have significantly higher cardiotonic activity than the corresponding known des-alkyl compounds, 3-amino-5-(4-pyridinyl)-2(1H)pyridinone, known as amrinone, and 1,2-dihydro-2-oxo-5-(4-pyridinyl)nicotinonitrile.

In a process aspect the invention resides in the process of producing 1-$R_1$-3-amino-5-PY-6-R-2(1H)-pyridinone (I, Q is amino) which comprises hydrolyzing 1-$R_1$-1,2-dihydro-2-oxo-5-PY-6-R-nicotinonitrile (I, Q is cyano) to produce the corresponding 3-carbamyl compounds (I, Q is carbamyl) and reacting the latter with a compound capable of converting carbamyl to amino, where $R_1$, PY and R are defined as hereinabove for I. Other process aspects resides in each of two steps, that is, the preparation of I where Q is carbamyl from I where Q is cyano and the conversion of I where Q is carbamyl to produce I where Q is amino.

In another process aspect the invention resides in the process of reacting PY-methyl lower-alkyl ketone of the formula PY—$CH_2$—C(=O)—R (II) with dimethylformamide di(lower-alkyl) acetal to produce 1-PY-2-(dimethylamino)ethenyl lower-alkyl ketone of the formula III

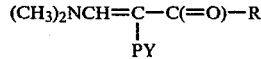

$$(CH_3)_2NCH=\underset{PY}{C}-C(=O)-R \qquad III$$

and reacting III with N-$R_1$-α-cyanoacetamide to produce 1-$R_1$-1,2-dihydro-2-oxo-5-PY-6-R-nicotinonitrile (I, Q is cyano), where PY, R, $R_1$ and R' have the meanings given for formula I.

Another composition of matter aspect of the invention resides in the 1-(pyridinyl)-2-(dimethylamino)ethenyl lower-alkyl ketones of formula III (supra) where PY and R have the meanings given for formula I, or pharmaceutically-acceptable acid-addition salt thereof.

In another process aspect the invention resides in the process which comprises reacting 1-$R_1$-5-PY-6-(lower-alkyl)-2(1H)-pyridinone (I where Q is hydrogen) with halogen, preferably bromine or chlorine, to produce the corresponding 3-halo compound (I, Q is halo) and reacting said 3-halo compound with a lower-alkylamine or a di-(lower-alkyl)amine to produce, respectively, the corresponding 3-(lower-alkyl)amino or 3-[di-(lower-alkyl)amino] compound [I, Q is lower-alkylamino or di-(lower-alkyl)amino, respectively].

An alternative process aspect of the invention for preparing I where Q is lower-alkylamino or di-(lower-alkyl)amino resides in the process which comprises reacting I where Q is amino with one or two molar equivalents of a lower-alkylating agent. A preferred embodiment of this alternative process comprises reacting I where Q is amino with a methylating mixture of formic acid and formaldehyde to produce I where Q is dimethylamino.

In another process aspect the invention resides in the process which comprises reacting I where Q is amino with a lower-acylating agent to produce I where Q is lower-acylamino.

A composition aspect of the invention resides in a cardiotonic composition for increasing cardiac contractility, said composition comprising a pharmaceutically-acceptable carrier and, as the active component thereof, an effective amount of a cardiotonic 1-$R_1$-3-Q-5-PY-6-R-2(1H)-pyridinone having the formula I, where $R_1$, Q, PY and R are each defined as in formula I or pharmaceutically-acceptable acid-addition or cationic salt thereof.

A method aspect of the invention resides in the method for increasing cardiac contractility in a patient requiring such treatment which comprises administering to such patient an effective amount of a cardiotonic 1-$R_1$-3-Q-5-PY-6-R-2(1H)-pyridinone having formula I, where $R_1$, Q, PY and R are each defined as in formula I, or pharmaceutically-acceptable acid-addition or cationic salt thereof.

The term "lower-alkyl" as used herein, e.g., as the meaning of R, as one of the meanings of $R_1$, as the meaning of "lower-alkyl" in lower-alkylamino or di-(lower-alkyl)amino as a meaning for Q or as a substituent for PY in formula I, means alkyl radicals having from 1 to 6 carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

The term "lower-hydroxyalkyl", as used herein, e.g., as one of the meanings for $R_1$ in formula I, means hydroxyalkyl radicals having from two to six carbon atoms and having its hydroxy group and its free valence bond (or connecting linkage) on different carbon atoms, illustrated by 2-hydroxyethyl, 2-hydroxypropyl, 3-hydroxypropyl, 2-hydroxy-2-methylpropyl, 2-hydroxy-1,1-dimethylethyl, 4-hydroxybutyl, 5-hydroxypentyl, 6-hydroxyhexyl, and the like.

Illustrative of PY in formula I where PY is 4-, 3- or 2-pyridinyl having 1 or 2 lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 4-methyl-2-pyridinyl, 6-methyl-2-pyridinyl, 2,3-dimethyl-4-pyridinyl, 2,6-dimethyl-4-pyridinyl, 4,6-dimethyl-2-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The term "lower-acyl", as used herein, e.g., as in the 3-(lower-acylamino) substituent in the compounds of formula I (Q is lower-acylamino), means alkanoyl radicals having from one to six carbon atoms, preferably one to four, and having substituents selected from hydroxy, acetoxy or propionoxy, including the straight- and branch-chained radicals, illustrated by formyl, acetyl, propionyl (n-propanoyl), butyryl (n-butanoyl), isobutyryl (2-methyl-n-propanoyl), caproyl (n-hexanoyl), hydroxyacetyl, α-hydroxypropionyl, β-hydroxypropionyl, α-acetoxypropionyl, propionoxyacetyl, β-acetoxypropionyl, α-acetoxybutyryl, and the like.

The compounds of formulas I and III are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base (I) are not vitiated by side effects ascribable to the anions. In practicing the invention, it is convenient to use the free base form; however, appropriate pharmaceutically-acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compound (I or III) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound (I or III) are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

Other pharmaceutically-acceptable salts of said compound of formula I are those cationic salts derived from strong inorganic or organic bases, e.g., sodium hydroxide, potassium hydroxide, trimethylammonium hydroxide, to produce the corresponding 1- or N-cationic salt, e.g., sodium, potassium, trimethylammonium salt, respectively, that is, the cationic ion being attached to the 1- or N-position of the 2(1H)-pyridinone ring.

The molecular structures of the compounds of formulas I and III were assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same, as follows.

The preparation of 1-PY-2-(dimethylamino)ethenyl lower-alkyl ketone (III) by reacting PY-methyl lower-alkyl ketone (II) with dimethylformamide di-(lower-alkyl) acetal is carried out by mixing the reactants in the presence or absence of a suitable solvent. The reaction is conveniently run at room temperature, i.e., about 20°–25° C., or by warming the reactants up to about 100° C., preferably in an aprotic solvent, conveniently hexamethylphosphoramide because of the method used to prepare the PY-methyl lower-alkyl ketone, as noted below in Example A-1. Other suitable solvents include tetrahydrofuran, dimethylformamide, acetonitrile, ether, benzene, dioxane, and the like. Also, the reaction can be run using no solvent, preferably using an excess of dimethylformamide di-(lower-alkyl)acetal. This procedure is further illustrated hereinbelow in Examples A-1 through A-17.

The intermediate PY-methyl lower-alkyl ketones (II) are generally known compounds which are prepared by known methods [e.g., as given in Rec. trav. chim 72, 522 (1953); U.S. Pat. No. 3,133,077 (May 12, 1964); Bull. Soc. Chim 1968, 4132; Chem. Abstrs. 79, 8539h (1973); Chem. Abstrs. 81, 120,401a (1974); J. Org. Chem. 39, 3834 (1974); Chem. Abstrs. 87, 6594q (1977); J. Org. Chem. 43, 2286 (1978)].

The reaction of 1-PY-2-(dimethylamino)ethenyl lower-alkyl ketone (III) with N-$R_1$-α-cyanoacetamide to produce 1-$R_1$-1,2-dihydro-2-oxo-5-PY-6-R-nicotinonitrile (I where Q is CN) is carried out preferably by heating the reactants in a suitable solvent in the presence of a basic condensing agent. The reaction is conveniently run using an alkali lower-alkoxide, preferably sodium methoxide or ethoxide, in dimethylformamide. In practicing the invention, the reaction was carried out in refluxing dimethylformamide using sodium methoxide. Alternatively, methanol and sodium methoxide or ethanol and sodium ethoxide can be used as solvent and basic condensing agent, respectively; however, a longer heating period is required. Other basic condensing agents and solvents include sodium hydride, lithium diethylamide, lithium diisopropylamide, and the like, in an aprotic solvent, e.g., tetrahydrofuran, acetonitrile, ether, benzene, dioxane, and the like. This procedure is further illustrated hereinbelow in Examples B-1 through B-21.

The partial hydrolysis of 1-$R_1$-1,2-dihydro-2-oxo-5-PY-6-R-nicotinonitrile (I where Q is cyano) to produce 1,2-dihydro-2-oxo-5-PY-6-R-nicotinamide (I where Q is carbamyl) is carried out by heating it (I where Q is cyano) with concentrated sulfuric acid. While the reaction is conveniently and preferably run by heating the reactants on a steam or oil bath at about 90°–100° C., the temperature range for the reaction can vary from about 70° to 120° C. This procedure is further illustrated hereinbelow in Examples C-1 through C-21.

The conversion of 1-$R_1$-1,2-dihydro-2-oxo-5-PY-6-R-nicotinamide (I where Q is carbamyl) to 1-$R_1$-3-amino-5-PY-6-R-2(1H)-pyridinone (I where Q is amino) is carried out by reacting it (I where Q is carbamyl) with a reagent capable of converting carbamyl to amino, e.g., an alkali metal hypohalite, lead tetraacetate. This reaction is conveniently run by heating an aqueous mixture containing an alkali metal hypohalite, preferably, sodium hypobromite or hypochlorite, and I where Q is carbamyl, and then acidifying the reaction mixture, preferably with an aqueous mineral acid, e.g., hydrochloric acid. The reaction can be run from about 40° C. to 100° C., preferably from 70° C. to 100° C. This procedure is further illustrated hereinbelow in Examples D-1 through D-21.

The conversion of 1-$R_1$-1,2-dihydro-2-oxo-5-PY-6-R-nicotinonitrile (I, Q is cyano) to 1-$R_1$-5-PY-6-R-2(1H)pyridinone (I, Q is hydrogen) is carried out by heating I where Q is cyano as above with an aqueous mineral acid, preferably 50% sulfuric acid, first to form I where Q is carboxy and then continue heating for a longer period whereupon the 3-carboxylic acid is decarboxylated to produce I where Q is hydrogen. This procedure is further illustrated hereinbelow in Examples E-1 through E-21.

The reaction 1-$R_1$-5-PY-6-R-2(1H)-pyridinone (I, Q is hydrogen) with halogen to produce the corresponding 3-halo compound (I, Q is halo) is carried out by mixing the reactants in an appropriate solvent inert under the reaction conditions, a preferred solvent being acetic acid. The reaction is conveniently run at room temperature or by heating the reactants at temperatures up to about 100° C. Preferred halogens are bromine and chlorine. Any inert solvent can be used, e.g., dimethylformamide, chloroform, acetic acid, and the like. This procedure is further illustrated hereinbelow in Examples F-1 through F-22.

The reaction of 1-$R_1$-3-halo-5-PY-2(1H)-pyridinone (I, Q is halo) with a lower-alkylamine or a di-(lower-alkyl)amine to produce the corresponding 1-$R_1$-3-(lower-alkylamino)-5-PY-6-R-2(1H)-pyridinone (I, Q is lower-alkylamino) or 1-$R_1$-3-[di-(lower-alkyl)amino]-5-PY-2(1H)-pyridinone [I, Q is di-(lower-alkyl)amino] is carried out by heating the reactants in an autoclave at about 110°–180° C., preferably about 145°–165° C. and preferably in a suitable solvent, e.g., water, dimethylformamide, dioxane, 1,2-dimethoxyethane, and the like, or mixtures thereof. This procedure is further illustrated hereinbelow in Examples G-1, G-2, G-3 to G-7, G-9 to G-19 and G-21 to G-23.

A preferred method of preparing 1-$R_1$-3-dimethylamino-5-PY-6-R-2(1H)-pyridinone (I, Q is dimethylamino) is carried out by reacting 1-$R_1$-3-amino-5-PY-6-R-2(1H)-pyridinone (I, Q is amino) with a mixture of formaldehyde and formic acid. This reaction is conveniently run by refluxing the 3-amino compound with an excess each of formaldehyde, preferably an aqueous solution thereof, and formic acid, preferably more than a two-fold molar excess of each. This procedure is further illustrated hereinbelow in Example G-3, G-8 and G-20.

The acylation of 1-$R_1$-3-amino-5-PY-6-R-2(1H)-pyridinone (I, Q is amino) to produce the corresponding 3-(lower-acylamino) compound (I, Q is lower-acylamino) is carried out by reacting I where Q is amino with a lower-acylating agent, e.g., a lower-acyl halide, preferably chloride, a lower-acyl anhydride, and the like, preferably in the presence of an acid-acceptor. The acid-acceptor is a basic substance which preferably forms freely water-soluble by-products easily separable from the product of the reaction, including for example, sodium hydroxide, potassium hydroxide, sodium carbonate, potassium carbonate, sodium alkoxides, potassium alkoxides, sodium amide, and the like. The reaction is preferably run in the presence of a suitable solvent which is inert under the reaction conditions, e.g., a solvent such as a lower-alkanol, acetone, dioxane, dimethylformamide, dimethyl sulfoxide, hexamethyl phosphoramide, or a mixture of solvents, e.g., a mixture of water and methylene dichloride or chloroform. The reaction is generally carried out at a temperature between about 10° C. and 150° C., preferably about 20°–25° C. This procedure is further illustrated hereinbelow in Examples H-1 through H-17.

The following examples will further illustrate the invention without, however, limiting it thereto.

A. 1-PY-2-(DIMETHYLAMINO)ETHENYL LOWER ALKYL KETONES

A-1.—1-(4-Pyridinyl)-2-(dimethylamino)ethenyl methyl ketone—A mixture containing 20 g. of (4-pyridinyl)methyl methyl ketone [alternatively named 1-(4-pyridinyl)-2-propanone] and 30 cc. of hexamethylphosphoramide was diluted with 65 cc. of dimethylformamide dimethyl acetal and the resulting mixture was refluxed for 30 minutes. TLC analysis showed a single spot, thereby indicating completion of the reaction (in another run, the reaction appeared to be complete after 30 minutes at room temperature). The reaction mixture was evaporated under reduced pressure using a rotary evaporator and a pressure of about 15 mm., thereby resulting in a crystalline residue weighing 24 g. The residue was purified by continuous chromatographic extraction on alumina (about 150 g.) using refluxing chloroform as eluant. After 1 and ½ hours, the extract was heated in vacuo to remove the chloroform, thereby leaving, as a light yellow crystalline material, 23.2 g. of 1-(4-pyridinyl)-2-(dimethylamino)ethenyl methyl ketone, alternatively named 4-dimethylamino-2-(4-pyridinyl)-3-buten-2-one.

The above preparation can be carried out using in place of hexamethylphosphoramide other solvents, e.g., dimethylformamide, acetonitrile or others noted above or in the absence of a solvent; however, hexamethylphosphoramide was conveniently used since (4-pyridinyl)methyl methyl ketone was conveniently prepared as a mixture together with hexamethylphosphoramide, as seen by the following preparation: To a stirred solution containing 70 cc. of freshly distilled diisopropylamine and 200 cc. of tetrahydrofuran at 0° C. under nitrogen was added dropwise over 20 minutes 210 cc. of 2.4 M n-butyllithium in n-hexane and the reaction mixture was stirred for about 35 minutes at about 0°–5° C. To the cold solution was added dropwise over a period of 10 minutes 90 cc. of dry hexamethylphosphoramide (no temperature change) and a resulting light yellow solution was stirred for 15 minutes. To the cold solution at 0° C. was added a solution of 50 cc. of 4-picoline in 150 cc. of dry tetrahydrofuran over a 15 minute period and stirring was continued for 30 minutes at 0° C. Next, a mixture containing 50 cc. of dry ethyl acetate and 150 cc. of tetrahydrofuran was added over a 15 minute period (temperature rose from 0° to about 6° C.) and the resulting mixture was stirred for 20 minutes at 0° C. The ice bath was then removed and stirring continued for another 90 minutes whereupon the temperature of the reaction mixture rose to about 25° C. The reaction mixture was then cooled in an ice bath and to it was added 60 cc. of acetic acid over a period of about 30 minutes. The tetrahydrofuran was distilled off using a rotary evaporator in vacuo. The remaining mixture was diluted with 400 cc. of water and the aqueous mixture was extracted successively with two 250 cc. portions of isopropyl acetate and three 80 cc. portions of chloroform. The solvents were distilled off under reduced pressure to yield about 137 g. of a mixture consisting primarily of the desired product and hexamethylphosphoramide. Another run using the same quantitites was carried out as above except after the addition of 60 cc. of glacial acetic acid, the mixture was diluted with only 200 cc. of water, the phases were separated, and the aqueous phase was extracted with five 100 ml. portions of chloroform. The chloroform extract was washed with saline solution and the chloroform was distilled off in vacuo. The remaining mixture of the desired ketone and hexamethylphosphoramide was combined with the above 137 g. of the same mixture and the combined mixture was distilled under reduced pressure to yield the following fractions: I. 63 g., b.p. of 110°–112° C. at 4 mm.; II. 59 g. of pale yellow oil, b.p. 113°–115° C. at 3 mm.; and, III. 69 g. of pale yellow oil, b.p. 115°–118° C. at 2.5 mm. Examination of fraction III by NMR showed it to consist of a 2:3 mixture by weight of (4-pyridinyl)methyl methyl ketone and hexamethylphosphoramide.

Acid-addition salts of 1-(4-pyridinyl)-2-(dimethylamino)ethenyl methyl ketone are conveniently prepared by adding to a mixture of 5 g. of 1-(4-pyridinyl)-2-(dimethylamino)ethenyl methyl ketone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1-(4-pyridinyl)-2-(dimethylamino)ethenyl methyl ketone and the appropriate acid, e.g., lactic acid or hydrochloric acid, to prepare respectively the monolactate or monohydrochloride salt in aqueous solution.

A-2.—1-(4-Pyridinyl)-2-(dimethylamino)ethenyl ethyl ketone—A mixture containing 87.5 g. of (4-pyridinyl)methyl ethyl ketone [alternatively named 1-(4-pyridinyl)-2-butanone] and 160 cc. of hexamethylphosphoramide was diluted with 100 g. of dimethylformamide dimethyl acetal and the resulting mixture was stirred under nitrogen at room temperature for 45 minutes. The methanol formed by the reaction was distilled off in vacuo using a rotary evaporator and the remaining material was distilled under reduced pressure to yield two fractions, one boiling at 45°–80° C. at 0.5 mm. and the second at 90°–95° C. at 0.5 mm. After TLC analysis showed predominantly only a single spot for each fraction, the two fractions were combined (135 g.) and taken up in 600 cc. of chloroform. The resulting solution was washed with two 300 cc. portions of water and the water was back extracted with three 100 cc. portions of chloroform. The combined chloroform solution was dried over anhydrous sodium sulfate and purified by continuous extraction chromatography on 300 cc. of alumina using refluxing chloroform as the eluant. The chloroform was distilled off in vacuo to yield a red oil which crystallized on standing overnight in an ice bath. The crystalline material was dissolved in carbon tetrachloride, cyclohexane was added and the mixture cooled to yield 64 g. of the resulting yellow crystalline product, 1-(4-pyridinyl)-2-(dimethylamino)ethenyl ethyl ketone. Another 11 g. of crystalline product was obtained from the mother liquor by continuous extraction chromatography on alumina using refluxing chloroform as the eluant.

The above intermediate (4-pyridinyl)methyl ethyl ketone was obtained in a mixture with hexamethylphosphoramide as follows: To a mixture containing 200 cc. of tetrahydrofuran and 70 cc. of diisopropylamine under nitrogen at 0°–5° C. was added 210 cc. of 2.4 N n-butyllithium in n-hexane and the resulting mixture was stirred for 30 minutes. Next was added over a 10 minute period 90 cc. of hexamethylphosphoramide followed by stirring of the mixture for 15 minutes. Then was added over a 15 minute period a solution of 48 cc. of 4-picoline in 150 cc. of tetrahydrofuran followed by stirring for 30 minutes at about 0° C. The ice/acetone bath cooling the reaction mixture was replaced with a dry ice/acetone bath and to the reaction mixture was added over a 20 minute period a mixture of 75 cc. of ethyl propionate in an equal volume of tetrahydrofuran. The reaction mixture was then allowed to warm up to room temperature over a period of about 90 minutes and then was warmed at about 35° C. for 30 minutes. The mixture was next cooled in an ice/acetone bath and to it was added 60 cc. of glacial acid over 30 minutes. The resulting pale yellow suspension was diluted with 200 cc. of water. The mixture was extracted with three 150 cc. portions of ethyl acetate and the ethyl acetate extract was back washed with saline solution. The extract was heated in vacuo to remove the ethyl acetate and the residue was taken up again with ethyl acetate. The solution was washed with water and then heated in vacuo to remove the ethyl acetate followed by heating the residue in vacuo at 50° C. for about 30 minutes to yield 100 g. of pale yellow oil. The pale yellow oil was combined with corresponding samples obtained from two additional runs and then distilled in vacuo to yield a 256 g. fraction, b.p. 85°–105° C. at 0.5–1.0 mm. The NMR of this fraction showed it to be a mixture of (4-pyridinyl)methyl ethyl ketone and hexamethylphosphoramide in a respective molar ratio of 1:1.55, that is, 35% or $0.35 \times 256 = 90$ g. of said ketone.

A-3. 1-(4-Pyridinyl)-2-(dimethylamino)ethenyl n-propyl ketone—A mixture containing 80 g. of (4-pyridinyl)methyl n-propyl ketone [alternatively named 1-(4-pyridinyl)-2-pentanone] and 46 cc. of hexamethylphosphoramide was diluted with 250 cc. of acetonitrile. To the mixture was added 90 cc. of dimethylformamide dimethyl acetal and the resulting reaction mixture was heated on a steam bath for ninety minutes and then distilled under vacuum at about 2 mm. to remove volatile materials, including methanol, acetonitrile and hexamethylphosphoramide. The remaining residue was diluted with ethyl acetate and washed with water. The combined water washings were extracted with five 150 cc. portions of ethyl acetate. The combined ethyl acetate solutions were washed with saline solution, dried over anhydrous sodium sulfate, filtered and evaporated to dryness. The residue crystallized while standing in a freezer. The crystalline product was slurried with cyclohexane, filtered and dried overnight at 30° C. to produce, as a yellow crystalline product, 97 g. of 1-(4-pyridinyl)-2-(dimethylamino)ethenyl n-propyl ketone, m.p. 48°–50° C.

The above intermediate (4-pyridinyl)methyl n-propyl ketone was obtained in a mixture with hexamethylphosphoramide as follows: To a stirred solution of 70 cc. of diisopropylamine in 200 cc. of tetrahydrofuran under nitrogen at about 0° C. (use of ice bath) was added 210 cc. of 2.4 N n-butyllithium over twenty minutes and the resulting mixture was stirred for 30 minutes at about 0° C. to the mixture was added with stirring over ten minutes 90 cc. of hexamethylphosphoramide and the resulting mixture was stirred for another ten minutes. Next 45 cc. of 4-picoline in 140 cc. of tetrahydrofuran was added dropwise over fifteen to twenty minutes. The resulting dark orange-brown solution was stirred at 0° C. for thirty minutes and then treated dropwise over an eighteen minute period a solution consisting of 68 cc. of ethyl butyrate in 68 cc. of tetrahydrofuran, the temperature rising from −8° C. to +8° to 10° C. The reaction mixture was removed from the ice bath and allowed to warm up to room temperature for over seventy-five minutes. The reaction mixture was re-cooled and to it was added dropwise over fifteen minutes 60 cc. of glacial acetic acid. A pale yellow solid separated, resulting in a suspension. The suspension was diluted with water and extracted with two 200 cc. portions of ethyl acetate. The ethyl acetate extract was washed with three 100 cc. portions of saline solution, dried over anhydrous sodium sulfate and evaporated in vacuo to yield 107 g. of a mixture consisting primarily of (4-pyridinyl)methyl n-propyl ketone and hexamethylphosphoramide. The mixture obtained in this run was combined with corresponding mixtures obtained in two other runs and the combined mixtures were distilled under vacuum to produce, as the major fraction, b.p. 80°-90° C. at 0.2 mm., a mixture consisting of 80 g. of (4-pyridinyl)-methyl n-propyl ketone and 46 g. of hexamethylphosphoramide.

Following the procedure described in Example A-2 but using a molar equivalent quantity of the appropriate PY-methyl lower-alkyl ketone (II) in place of (4-pyridinyl)methyl ethyl ketone, it is contemplated that the corresponding 1-PY-2-(dimethylamino)ethenyl lower-alkyl ketones of Examples A-4 thru A-17 can be obtained.

A-4. 1-(3-Pyridinyl)-2-(dimethylamino)ethenyl methyl ketone using (3-pyridinyl)methyl methyl ketone.

A-5. 1-(2-Pyridinyl)-2-(dimethylamino)ethenyl methyl ketone using (2-pyridinyl)methyl methyl ketone.

A-6. 1-(4-Pyridinyl)-2-(dimethylamino)ethenyl isopropyl ketone using (4-pyridinyl)methyl isopropyl ketone.

A-7. 1-(4-Pyridinyl)-2-(dimethylamino)ethenyl n-butyl ketone using (4-pyridinyl)methyl n-butyl ketone.

A-8. 1-(4-Pyridinyl)-2-(dimethylamino)ethenyl isobutyl ketone using (4-pyridinyl)methyl isobutyl ketone.

A-9. 1-(4-Pyridinyl)-2-(dimethylamino)ethenyl tert.-butyl ketone using (4-pyridinyl)methyl tert.-butyl ketone.

A-10. 1-(4-Pyridinyl)-2-dimethylamino)ethenyl n-pentyl ketone using (4-pyridinyl)methyl n-pentyl ketone.

A-11. 1-(2-Methyl-4-pyridinyl)-2-(dimethylamino)ethenyl ethyl ketone using (2-methyl-4-pyridinyl)methyl ethyl ketone.

A-12. 1-(5-Methyl-2-pyridinyl)-2-dimethylamino)ethenyl methyl ketone using (5-methyl-2-pyridinyl)methyl methyl ketone.

A-13. 1-(5-Ethyl-2-pyridinyl)-2-(dimethylamino)ethenyl ethyl ketone using (5-ethyl-2-pyridinyl)methyl ethyl ketone.

A-14. 1-(3-Pyridinyl)-2-(dimethylamino)ethenyl ethyl ketone using (3-pyridinyl)methyl ethyl ketone.

A-15. 1-(4,6-Dimethyl-2-pyridinyl)-2-(dimethylamino)ethenyl methyl ketone using (4,6-dimethyl-2-pyridinyl)methyl methyl ketone.

A-16. 1-(6-Methyl-2-pyridinyl)-2-(dimethylamino)ethenyl isopropyl ketone using (6-methyl-2-pyridinyl)methyl isopropyl ketone.

A-17. 1-(2-Pyridinyl)-2-(dimethylamino)ethenyl n-hexyl ketone using (2-pyridinyl)methyl n-hexyl ketone.

B.
1-$R_1$-1,2-DIHYDRO-6-(LOWER-ALKYL)-2-OXO-5-PY-NICOTINONITRILES

B-1.—1,2-Dihydro-6-methyl-2-oxo-5-(4-pyridinyl)-nicotinonitrile, alternatively named 1,6-dihydro-2-methyl-6-oxo-[3,4'-bipyridine]-5-carbonitrile— To a mixture containing 23 g. of 1-(4-pyridinyl)-2-(dimethylamino)ethenyl methyl ketone and 11 g. of α-cyanoacetamide dissolved in 400 cc. of dimethylformamide was added with stirring 14 g. of sodium methoxide and the resulting reaction mixture was heated in an oil bath under gentle reflux for one hour. TLC analysis showed no starting material in the reaction mixture which was then concentrated in vacuo on a rotary evaporator to a volume of about 80 cc. The concentrate was treated with about 160 cc. of acetonitrile and the resulting mixture was stirred on a rotary evaporator with warming until homogenous and then cooled. The crystalline product was collected, rinsed successively with acetonitrile and ether, and dried overnight at 55° C. to yield 28 g. of tan crystalline product, namely, sodium salt of 1,2-dihydro-6-methyl-2-oxo-5-(4-pyridinyl)nicotinonitrile, the presence of cyano being confirmed by IR analysis. An 8 g. portion of said sodium salt was dissolved in 75 cc. of hot water, the aqueous solution treated with decolorizing charcoal filtered, the filtrate again treated with decolorizing charcoal and filtered, and the filtrate acidified with 6 N-hydrochloric acid by dropwise addition to a pH of 3. The acidic mixture was diluted with ethanol and cooled. The crystalline product was collected, dried, recrystallized from dimethylformamide-water and dried to produce 3.75 g of 1,2-dihydro-6-methyl-2-oxo-5-(4-pyridinyl)-nicotinonitrile, m.p. >300° C.

Acid-addition salts of 1,2-dihydro-6-methyl-2-oxo-5-(4-pyridinyl)nicotinonitrile are conveniently prepared by adding to a mixture of 2 g. of 1,2-dihydro-6-methyl-2-oxo-5-(4-pyridinyl)nicotinonitrile in about 40 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1,2-dihydro-6-methyl-2-oxo-5-(4-pyridinyl)nicotinonitrile and the appropriate acid, e.g., lactic acid or hydrochloric acid, to prepare respectively the monolactate or monohydrochloride salt in aqueous solution.

B-2.—6-Ethyl-1,2-dihydro-2-oxo-5-PY-nicotinonitrile, alternatively named 2-ethyl-1,6-dihydro-6-oxo-[3,4'-bipyridine]-5-carbonitrile, m.p. >300° C., 11.6 g., was prepared following the procedure described above in Example B-1 using 20 g. of 1-(4-pyridinyl)-2-(dimethylamino)ethenyl ethyl ketone, 8.4 g. of α-cyanoacetamide, 16.2 g. of sodium methoxide and 250 cc. of dimethylacetamide (as solvent in place of dimethylformamide).

B-3.—1,2-Dihydro-2-oxo-6-n-propyl-5-(4-pyridinyl)-nicotinonitrile, alternatively named 1,6-dihydro-6-oxo-2-n-propyl-[3,4'-bipyridine]-5-carbonitrile, m.p. 232°-234° C., 9.9 g., was prepared following the procedure described above in Example B-1 using 85 g. of 1-(4-pyridinyl)-2-(dimethylamino)ethenyl n-propyl ketone, 36.5 g. of α-cyanoacetamide, 50 g. of sodium methoxide and 800 cc. of dimethylacetamide.

B-4.—1,2-Dihydro-1,6-dimethyl-2-oxo-5-(4-pyridinyl)nicotinonitrile, alternatively named 1,6-dihydro-1,2-dimethyl-6-oxo-(3,4'-bipyridine)-5-carbonitrile, m.p. 245°–248° C., 32.3 g., was prepared following the procedure described above in Example B-1 using 42.5 g. of 1-(4-pyridinyl)-2-(dimethylamino)ethenyl methyl ketone, 23.5 g. of N-methyl-α-cyanoacetamide, 6.7 g. of sodium methoxide, 400 ml. of methanol and a refluxing period of two hours.

Following the procedure described in Example B-2 but using a molar equivalent quantity of the appropriate 1-PY-2-(dimethylamino)ethenyl lower-alkyl ketone (III) in place of 1-(4-pyridinyl)-2-(dimethylamino)ethenyl ethyl ketone and the appropriate N-$R_1$-α-cyanoacetamide, it is contemplated that the corresponding 1-$R_1$-1,2-dihydro-2-oxo-5-PY-6-R-nicotinonitriles of Examples B-5 thru B-21 can be obtained.

B-5. 1,2-Dihydro-6-methyl-2-oxo-5-(3-pyridinyl)nicotinonitrile, using 1-(3-pyridinyl)-2-(dimethylamino)ethenyl methyl ketone and α-cyanoacetamide.

B-6. 1,2-Dihydro-6-methyl-2-oxo-5-(2-pyridinyl)nicotinonitrile, using 1-(2-pyridinyl)-2-(dimethylamino)ethenyl methyl ketone and α-cyanoacetamide.

B-7. 1,2-Dihydro-6-isopropyl-2-oxo-5-(4-pyridinyl)nicotinonitrile, using 1-(4-pyridinyl)-2-(dimethylamino)ethenyl isopropyl ketone and α-cyanoacetamide.

B-8. 6-n-Butyl-1,2-dihydro-2-oxo-5-(4-pyridinyl)nicotinonitrile, using 1-(4-pyridinyl)-2-(dimethylamino)ethenyl n-butyl ketone and α-cyanoacetamide.

B-9. 1,2-Dihydro-6-isobutyl-2-oxo-5-(4-pyridinyl)nicotinonitrile, using 1-(4-pyridinyl)-2-(dimethylamino)ethenyl isobutyl ketone and α-cyanoacetamide.

B-10. 1,2-Dihydro-2-oxo-5-(4-pyridinyl)-6-tert.-butylnicotinonitrile, using 1-(4-pyridinyl)-2-(dimethylamino)ethenyl tert.-butyl ketone and α-cyanoacetamide.

B-11. 1,2-Dihydro-2-oxo-6-n-pentyl-5-(4-pyridinyl)nicotinonitrile, using 1-(4-pyridinyl)-2-(dimethylamino)ethenyl n-pentyl ketone and α-cyanoacetamide.

B-12. 6-Ethyl-1,2-dihydro-5-(2-methyl-4-pyridinyl)-2-oxonicotinonitrile, using 1-(2-methyl-4-pyridinyl)-2-(dimethylamino)ethenyl ethyl ketone and α-cyanoacetamide.

B-13. 1,2-Dihydro-6-methyl-5-(5-methyl-2-pyridinyl)-2-oxonicotinonitrile, using 1-(5-methyl-2-pyridinyl)-2-(dimethylamino)ethenyl methyl ketone and α-cyanoacetamide.

B-14. 6-Ethyl-5-(5-ethyl-2-pyridinyl)-1,2-dihydro-2-oxonicotinonitrile, using 1-(5-ethyl-2-pyridinyl)-2-(dimethylamino)ethenyl ethyl ketone and α-cyanoacetamide.

B-15. 6-Ethyl-1,2-dihydro-2-oxo-5-(3-pyridinyl)nicotinonitrile, using 1-(3-pyridinyl)-2-(dimethylamino)ethenyl ethyl ketone and α-cyanoacetamide.

B-16. 1,2-Dihydro-5-(4,6-dimethyl-2-pyridinyl)-6-methyl-2-oxonicotinonitrile, using 1-(4,6-dimethyl-2-pyridinyl)-2-(dimethylamino)ethenyl methyl ketone and α-cyanoacetamide.

B-17. 1,2-Dihydro-6-isopropyl-5-(6-methyl-2-pyridinyl)-2-oxo-nicotinonitrile, using 1-(6-methyl-2-pyridinyl)-2-(dimethylamino)ethenyl isopropyl ketone and α-cyanoacetamide.

B-18. 1,2-Dihydro-6-n-hexyl-2-oxo-5-(2-pyridinyl)nicotinonitrile using 1-(2-pyridinyl)-2-(dimethylamino)ethenyl n-hexyl ketone and α-cyanoacetamide.

B-19. 6-Ethyl-1,2-dihydro-1-(2-hydroxyethyl)-2-oxo-5-(4-pyridinyl)nicotinonitrile, using 1-(4-pyridinyl)-2-(dimethylamino)ethenyl ethyl ketone and N-(2-hydroxyethyl)-α-cyanoacetamide.

B-20. 1-Ethyl-1,2-dihydro-6-methyl-2-oxo-5-(4-pyridinyl)nicotinonitrile, using 1-(4-pyridinyl)-2-(dimethylamino)ethenyl methyl ketone and N-ethyl-α-cyanoacetamide.

B-21. 1,6-Diethyl-1,2-dihydro-2-oxo-5-(4-pyridinyl)nicotinonitrile, using 1-(4-pyridinyl)-2-(dimethylamino)ethenyl ethyl ketone and N-ethyl-α-cyanoacetamide.

C.

1-$R_1$-1,2-DIHYDRO-6-(LOWER-ALKYL)-2-OXO-5-(PYRIDINYL)NICOTINAMIDES

C-1.—1,2-Dihydro-6-methyl-2-oxo-5-(4-pyridinyl)nicotinamide, alternatively named 1,2-dihydro-2-methyl-6-oxo-[3,4'-bipyridine]-5-carboxamide— A mixture containing 9.0 g. of 1,2-dihydro-6-methyl-2-oxo-5-(4-pyridinyl)nicotinonitrile and 45 cc. of concentrated sulfuric acid was heated at 100° C. for 30 minutes using an oil bath. The hot reaction mixture was added to 200 cc of ice and the resulting mixture cooled in an ice/acetone bath. To the cold solution was carefully added dropwise about 150 cc. of 28% ammonium hydroxide. The resulting mixture containing a precipitate was cooled in an ice/acetone bath for about 30 minutes. The precipitate was then collected, rinsed successively with water and acetonitrile, dried well and recrystallized by dissolving in 130 cc. of hot water (to boil), adding 30 cc. of acetic acid, treating with decolorizing charcoal and filtering. The filtrate was concentrated and diluted with acetonitrile; the mixture was kept in ice for about 30 minutes. The resulting crystalline material was collected to yield 8.35 g. of tan crystalline material. This material was combined with the same material obtained from another run and the combined 13.5 g. was dissolved in 500 cc. of dimethylformamide at its boiling point, the hot mixture filtered and the filtrate cooled in an ice bath. The crystalline precipitate was collected, rinsed with acetone and dried for 14 hours at 100° C. over $P_2O_5$ and found by its IR and NMR analyses to still contain some dimethylformamide. The 10.5 g. of buff colored crystalline product was dissolved in 75 cc. of hot acetic acid, treated with 50 cc. of water and then diluted to a volume of 300 cc. with acetone. The resulting mixture containing some crystals was cooled in an ice bath for about 45 minutes. The resulting light tan crystalline product was collected, dried first at 55° C. and then at 110° C. to remove the last faint odor of acetic acid to produce 9.2 g. of 1,2-dihydro-6-methyl-2-oxo-5-(4-pyridinyl)nicotinamide, m.p. >300° C.

Acid-addition salts of 1,2-dihydro-6-methyl-2-oxo-5-(4-pyridinyl)nicotinamide are conveniently prepared by adding to a mixture of 5 g. of 1,2-dihydro-6-methyl-2-oxo-5-(4-pyridinyl)nicotinamide in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1,2-dihydro-6-methyl-2-oxo-5-(4-pyridinyl)nicotinamide and the appropriate acid, e.g., lactic acid or hydrochloric acid, to prepare respectively the monolactate or monohydrochloride salt in aqueous solution.

C-2.—6-Ethyl-1,2-dihydro-2-oxo-5-(4-pyridinyl)-nicotinamide, alternatively named 1,6-dihydro-2-ethyl-6-oxo-[3,4'-bipyridine]-5-carboxamide— A 40 g. portion of 6-ethyl-1,2-dihydro-2-oxo-5-(4-pyridinyl)-nicotinonitrile was added to 170 cc. of concentrated sulfuric acid whereupon the temperature rose to about 70° C. This reaction mixture was immersed in a preheated oil bath at about 90° C. and then kept between 95°–105° C. for about 40 minutes. The hot reaction mixture was then poured into a beaker containing 800 cc. of ice. The mixture was stirred and then placed in an ice/acetone bath. To the cold mixture was added dropwise with stirring 650 cc. of 28% ammonium hydroxide whereupon the temperature rose to about 46° C. To the mixture was added with stirring about 300 cc. of ice and stirring was continued for about 15 minutes. The precipitate was collected, rinsed with three 150 cc. portions of water, air-dried for two hours, slurried with some acetonitrile, filtered and the solid dried for several days at 55° C. to yield 39.5 g. of product. The solid was stirred well with 300 cc. of water, filtered and dried to produce 38 g. of crystalline product, 6-ethyl-1,2-dihydro-2-oxo-5-(4-pyridinyl)nicotinamide. A 14.3 g. portion of this product was further purified by dissolving it in 40 cc. of hot acetic acid, filtering the hot solution and diluting the filtrate to 180 cc. of absolute ethanol whereupon crystals formed. The hot mixture was allowed to cool. The light tan crystalline product was collected and dried at 110° C. over $P_2O_5$ for about 15 hours to produce 11.7 g. of 6-ethyl-1,2-dihydro-2-oxo-5-(4-pyridinyl)nicotinamide, m.p. >300° C.

C-3. 1,2-Dihydro-2-oxo-6-n-propyl-5-(4-pyridinyl)-nicotinamide, alternatively named 1,6-dihydro-6-oxo-2-n-propyl-[3,4'-bipyridine]-5-carboxamide, m.p. >300° C., 10.5 g., was prepared following the procedure described in Example C-2 using 30.7 g. of 1,2-dihydro-2-oxo-6-n-propyl-5-(4-pyridinyl)nicotinonitrile and 130 cc. of concentrated sulfuric acid.

Following the procedure described in Example C-2 but using a molar equivalent quantity of the appropriate 1-$R_1$-1,2-dihydro-2-oxo-5-PY-6-R-nicotinonitrile (I where Q is cyano) in place of 6-ethyl-1,2-dihydro-2-oxo-5-(4-pyridinyl)nicotinonitrile, it is contemplated that the corresponding 1,2-dihydro-2-oxo-5-PY-6-R-nicotinamides of Examples C-4 thru C-21 can be obtained.

C-4. 1,2-Dihydro-6-methyl-2-oxo-5-(3-pyridinyl)-nicotinamide.

C-5. 1,2-Dihydro-6-methyl-2-oxo-5-(2-pyridinyl)-nicotinamide.

C-6. 1,2-Dihydro-6-isopropyl-2-oxo-5-(4-pyridinyl)-nicotinamide.

C-7. 6-n-Butyl-1,2-dihydro-2-oxo-5-5-(4-pyridinyl)-nicotinamide.

C-8. 1,2-Dihydro-6-isobutyl-2-oxo-5-(4-pyridinyl)-nicotinamide.

C-9. 1,2-Dihydro-2-oxo-5-(4-pyridinyl)-6-tert.-butyl-nicotinamide.

C-10. 1,2-Dihydro-2-oxo-6-n-pentyl-5-(4-pyridinyl)-nicotinamide.

C-11. 6-Ethyl-1,2-dihydro-5-(2-methyl-4-pyridinyl)-2-oxonicotinamide.

C-12. 1,2-Dihydro-6-methyl-5-(5-methyl-2-pyridinyl)-2-oxonicotinamide.

C-13. 6-Ethyl-5-(5-ethyl-2-pyridinyl)-1,2-dihydro-2-oxonicotinamide.

C-14. 6-Ethyl-1,2-dihydro-5-(3-pyridinyl)-2-oxonicotinamide.

C-15. 1,2-Dihydro-6-methyl-5-(4,6-dimethyl-2-pyridinyl)-2-oxonicotinamide.

C-16. 1,2-Dihydro-6-isopropyl-5-(6-methyl-2-pyridinyl)-2-oxonicotinamide.

C-17. 1,2-Dihydro-6-n-hexyl-2-oxo-5-(2-pyridinyl)-nicotinamide.

C-18. 1,2-Dihydro-1,6-dimethyl-2-oxo-5-(4-pyridinyl)nicotinamide.

C-19. 6-Ethyl-1,2-dihydro-1-(2-hydroxyethyl)-2-oxo-5-(4-pyridinyl)nicotinamide.

C-20. 1-Ethyl-1,2-dihydro-6-methyl-2-oxo-5-(4-pyridinyl)nicotinamide.

C-21. 1,6-Diethyl-1,2-dihydro-2-oxo-5-(4-pyridinyl)-nicotinamide.

D.
1-$R_1$-3-AMINO-6-(LOWER-ALKYL)-5-PY-2(1H)-PYRIDINONES

D-1. 3-Amino-6-methyl-5-(4-pyridinyl)-2(1H)-pyridinone, alternatively named 5-amino-2-methyl-[3,4'-bipyridin]-6(1H)-one— To a solution containing 13 g. of sodium hydroxide in 250 cc. of water was added 12 g. of 1,2-dihydro-6-methyl-2-oxo-5-(4-pyridinyl)nicotinamide and the resulting mixture was heated on a steam bath to effect dissolution. To the solution was added another 250 cc. of water and the resulting solution cooled to about 35° C. with stirring whereupon some crystals separated. The mixture was chilled in an ice bath and to it was added dropwise a total of 4.0 cc. of bromine, dissolution resulting after about 3 cc. of the bromine had been added. The mixture was stirred for an additional 10 minutes while cold and then was heated on a steam bath for 45 minutes. The reaction mixture was then concentrated to about ½ its volume, cooled in an ice bath and treated with 6 N hydrochloric acid until the pH was about 8. The resulting crystalline product was collected, rinsed twice with water and once with acetone, and dried to yield 7.3 g. of material. The 7.3 g. was treated with 20 cc. of water and the insoluble amorphous material was filtered off. The filtrate was concentrated to dryness and the resulting crystalline material was recrystallized from dimethylformamide-water to yield 3.8 g. of 3-amino-6-methyl-5-(4-pyridinyl)-2(1H)-pyridinone, m.p. >300° C.

Acid-addition salts of 3-amino-6-methyl-5-(4-pyridinyl)2(1H)-pyridinone are conveniently prepared by adding to a mixture of 2 g. of 3-amino-6-methyl-5-(4-pyridinyl)-2(1H)-pyridine in about 40 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 3-amino-6-methyl-5-(4-pyridinyl)-2(1H)-pyridinone and the appropriate acid, e.g., lactic acid or hydrochloric acid, to prepare respectively the monolactate or monohydrochloride salt in aqueous solution.

D-2. 3-Amino-6-ethyl-5-(4-pyridinyl)-2(1H)-pyridinone, alternatively named 5-amino-2-ethyl-[3,4'- bipyridin]-6(1H)-one, m.p. >300° C., 8.8 g., was prepared following the procedure described in Example D-1 but using 10.0 g. of 6-ethyl-1,2-dihydro-2-oxo-5-(4-pyridinyl)nicotinamide, 8.8 g. of sodium hydroxide, 300 cc. of water, 3.0 cc. of bromine, and recrystallization from dimethylformamide-isopropyl alcohol.

D-3. 3-Amino-6-n-propyl-5-(4-pyridinyl)-2-(1H)-pyridinone, alternatively named 5-amino-2-n-propyl-[3,4'-bipyridin]-6(1H)-one— To a stirred mixture containing 8.5 g. of 1,2-dihydro-2-oxo-6-n-propyl-5-(4-pyridinyl)nicotinamide and 95 cc. of water at room temperature was added a solution of 1.32 g. of sodium hydroxide in 6 cc. of water. The resulting slurry was cooled in an ice bath, stirred for ten minutes and then treated by dropwise addition of 22 cc. of 13.1% aqueous sodium hypochlorite over a three minute period. Dissolution resulted and stirring was continued without cooling for thirty minutes. To the resulting solution at 15° C. was added 27 cc. of 35% aqueous sodium hydroxide; the reaction mixture was warmed on a steam bath at about 60°–70° C. for one hour; and, the warm solution was treated slowly with 14 cc. of glacial acetic acid over a five minute period, whereupon a tan precipitate separated. The mixture was stirred for five minutes; the precipitate was collected, washed with warm water and dried over $P_2O_5$. The resulting 12 g. of product was recrystallized from dimethylformamide(100 cc.)-water(80 cc.), dried overnight at 95° C. over $P_2O_5$ to yield 9.5 g. of 3-amino-6-n-propyl-5-(4-pyridinyl)-2(1H)-pyridinone, m.p. 200°–202° C.

Following the procedure described in Example D-1 but using a molar equivalent quantity of the appropriate 1-$R_1$-1,2-dihydro-2-oxo-5-PY-6-R-nicotinamide (I where Q is carbamyl) in place of 1,2-dihydro-6-methyl-2-oxo-5-(4-pyridinyl)nicotinamide, it is contemplated that the corresponding 1-$R_1$-3-amino-5-PY-6-R-2-(1H)-pyridinones of Examples D-4 thru D-21 can be obtained.

D-4. 3-Amino-6-methyl-5-(3-pyridinyl)-2(1H)-pyridinone.

D-5. 3-Amino-6-methyl-5-(2-pyridinyl)-2(1H)-pyridinone.

D-6. 3-Amino-6-isopropyl-5-(4-pyridinyl)-2(1H)-pyridinone.

D-7. 3-Amino-6-n-butyl-5-(4-pyridinyl)-2(1H)-pyridinone.

D-8. 3-Amino-6-isobutyl-5-(4-pyridinyl)-2(1H)-pyridinone.

D-9. 3-Amino-6-tert.-butyl-5-(4-pyridinyl)-2(1H)-pyridinone. D-10. 3-Amino-6-n-pentyl-5-(4-pyridinyl)-2(1H)-pyridinone.

D-11. 3-Amino-6-ethyl-5-(2-methyl-4-pyridinyl)-2(1H)-pyridinone.

D-12. 3-Amino-6-methyl-5-(5-methyl-2-pyridinyl)-2(1H)-pyridinone.

D-13. 3-Amino-6-ethyl-5-(5-ethyl-2-pyridinyl)-2(1H)-pyridinone.

D-14. 3-Amino-6-ethyl-5-(3-pyridinyl)-2(1H)-pyridinone.

D-15. 3-Amino-6-methyl-5-(4,6-dimethyl-2-pyridinyl)-2(1H)-pyridinone.

D-16. 3-Amino-6-isopropyl-5-(6-methyl-2-pyridinyl)-2(1H)-pyridinone.

D-17. 3-Amino-6-n-hexyl-5-(2-pyridinyl)-2(1H)-pyridinone.

D-18. 3-Amino-1,6-dimethyl-5-(4-pyridinyl)-2(1H)-pyridinone.

D-19. 3-Amino-6-ethyl-1-(2-hydroxyethyl)-5-(4-pyridinyl)-2(1H)-pyridinone.

D-20. 3-Amino-1-ethyl-6-methyl-5-(4-pyridinyl)-2(1H)-pyridinone.

D-21. 3-Amino-1,6-diethyl-5-(4-pyridinyl)-2(1H)-pyridinone.

E.
1-$R_1$-6-(LOWER-ALKYL)-5-PY-2(1H)-PYRIDINONES

E-1. 6-Methyl-5-(4-pyridinyl)-2(1H)-pyridinone, alternatively named 2-methyl-[3,4'-bipyridin]-6(1H)-one —A mixture of 5.3 g. of 1,2-dihydro-6-methyl-2-oxo-5-(4-pyridinyl)nicotinonitrile and 30 cc. of 85% sulfuric acid was heated to about 195° C., gently refluxed for twenty-four hours, cooled and added to ice. The aqueous mixture was brought to a pH of 8 by addition of concentrated aqueous sodium hydroxide solution. The resulting precipitate (product plus $Na_2SO_4$) was treated with chloroform and the chloroform solution filtered. The filtrate was concentrated in vacuo to remove the chloroform and the resulting crystalline residue was recrystallized from methylene dichloride-ether and dried at 75° C. for four hours to produce 4.1 g. of 6-methyl-5-(4-pyridinyl)-2(1H)-pyridinone, m.p. 287°–288° C.

Acid-addition salts of 6-methyl 5-(4-pyridinyl)-2(1H)-pyridinone are conveniently prepared by adding to a mixture of 5 g. of 6-methyl-5-(4-pyridinyl)-2(1H)-pyridinone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 6-methyl-5-(4-pyridinyl)-2(1H)-pyridinone and the appropriate acid, e.g., lactic acid or hydrochloric acid, to prepare respectively the monolactate or monohydrochloride salt in aqueous solution.

E-2. 6-Ethyl-5-(4-pyridinyl)-2(1H)-pyridinone, alternatively named 2-ethyl-[3,4'-bipyridin]-6(1H)-one —A mixture containing 9 g. of 6-ethyl-1,2-dihydro-2-oxo-5-(4-pyridinyl)nicotinonitrile and 50 ml. of concentrated sulfuric acid was heated with stirring at 200° C. for twenty-four hours, cooled to about 40° C. and quenched in 200 ml. of ice water. After the aqueous solution had been basified with concentrated ammonium hydroxide, the separated solid was collected, recrystallized from isopropyl alcohol (70 ml.), and dried at 60° C. in vacuo to yield 3 g. of 6-ethyl-5-(4-pyridinyl)-2(1H)-pyridinone, m.p. 226°–228° C. A second crop of 0.4 g., m.p. 225°–227° C., was obtained by concentrating the filtrate to about 20 ml.

E-3. 6-n-Propyl-5-(4-pyridinyl)-2(1H)-pyridinone, alternatively named 2-(n-propyl)-[3,4'-bipyridin]-6(1H)-one, m.p. 179°–180° C., 3.4 g., was obtained following the procedure described in Example E-2 but using 10 g. of 1,2-dihydro-6-n-propyl-2-oxo-5-(4-pyridinyl)nicotinonitrile, 42.5 cc. of 85% sulfuric acid, and recrystallization from methylene dichloride-ether.

Following the procedure described in Example E-2 but using in place of 6-ethyl-1,2-dihydro-2-oxo-5-(4-pyridinyl)nicotinonitrile a molar equivalent quantity of the corresponding 1-$R_1$-1,2-dihydro-2-oxo-5-PY-6-(lower-alkyl)nicotinonitrile, it is contemplated that there can be obtained the 1-$R_1$-5-PY-6-(lower-alkyl)-2(1H)-pyridinones of Examples E-4 through E-21.

E-4. 6-Methyl-5-(3-pyridinyl)-2(1H)-pyridinone.
E-5. 6-Isopropyl-5-(4-pyridinyl)-2(1H)-pyridinone.
E-6. 6-n-Butyl-5-(4-pyridinyl)-2(1H)-pyridinone.
E-7. 6-Isobutyl-5-(4-pyridinyl)-2(1H)-pyridinone.
E-8. 5-(4-Pyridinyl)-6-tert.-butyl-2(1H)-pyridinone.
E-9. 6-n-Pentyl-5-(4-pyridinyl)-2(1H)-pyridinone.
E-10. 6-Ethyl-5-(2-methyl-4-pyridinyl)-2(1H)-pyridinone.
E-11. 6-Ethyl-5-(3-pyridinyl)-2(1H)-pyridinone.
E-12. 1,6-Dimethyl-5-(4-pyridinyl)-2(1H)-pyridinone.
E-13. 6-Ethyl-1-(2-hydroxyethyl)-5-(4-pyridinyl)-2(1H)-pyridinone.
E-14. 1-Ethyl-6-methyl-5-(4-pyridinyl)-2(1H)-pyridinone.
E-15. 1,6-Diethyl-5-(4-pyridinyl)-2(1H)-pyridinone.
E-16. 6-Methyl-5-(2-pyridinyl)-2(1H)-pyridinone.
E-17. 6-Methyl-5-(5-methyl-2-pyridinyl)-2(1H)-pyridinone.
E-18. 6-Ethyl-5-(5-ethyl-2-pyridinyl)-2(1H)-pyridinone.
E-19. 6-Methyl-5-(4,6-dimethyl-2-pyridinyl)-2(1H)-pyridinone.
E-20. 6-Isopropyl-5-(6-methyl-2-pyridinyl)-2(1H)-pyridinone.
E-21. 6-n-Hexyl-5-(2-pyridinyl)-2(1H)-pyridinone.

F.
1-$R_1$-3-HALO-6-(LOWER-ALKYL)-5-PY-2(1H)-PYRIDINONES

F-1. 3-Bromo-6-methyl-5-(4-pyridinyl)-2(1H)-pyridinone, alternatively named 5-bromo-2-methyl-[3,4'-bipyridin]-6(1H)-one—To a stirred solution of 80 g. of 6-methyl-5-(4-pyridinyl)-2(1H)-pyridinone in one liter of acetic acid heated at 65° C. was added dropwise over twenty-five minutes 69 g. of bromine in 50 cc. of acetic acid. The reaction mixture was stirred for an additional thirty minutes, cooled to room temperature and filtered to collect the crystalline precipitate. The precipitate was dried and suspended in 1500 cc. of water. To the vigorously stirred suspension was added dropwise 25 cc. of 28% ammonium hydroxide whereupon a white creamy precipitate separated. The solid was collected and dried in vacuo at 90° C. to yield 101 g. of 3-bromo-6-methyl-5-(4-pyridinyl)-2(1H)-pyridinone, m.p. 252°-254° C. A 15 g. sample was dissolved in 200 cc. of hot acetic acid and filtered. The filtrate was concentrated in vacuo, diluted with methanol, and the resulting white crystalline precipitate was collected, dried at 100° C. for sixteen hours in vacuo to yield 9.8 g. of said product, m.p. 252°-254° C.

Acid-addition salts of 3-bromo-6-methyl-5-(4-pyridinyl)-2(1H)-pyridinone are conveniently prepared by adding to a mixture of 5 g. of 3-bromo-6-methyl-5-(4-pyridinyl)-2(1H)-pyridinone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 3-bromo-6-methyl-5-(4-pyridinyl)-2(1H)-pyridinone and the appropriate acid, e.g., lactic acid or hydrochloric acid, to prepare respectively the monolactate or monohydrochloride salt in aqueous solution.

F-2. 3-Chloro-6-methyl-5-(4-pyridinyl)-2(1H)-pyridinone, alternatively named 5-chloro-2-methyl-[3,4'-bipyridin]-6(1H)-one—A mixture containing 18.6 g. of 6-methyl-5-(4-pyridinyl)-2(1H)-pyridinone and 200 ml. of acetic acid heated on a steam bath is treated by bubbling chlorine into it for four hours. After allowing the reaction mixture to cool to room temperature, the solid is collected, washed with ether and dried. The solid is dissolved in water, the aqueous solution is neutralized with 2 N aqueous potassium hydroxide solution, and the mixture is cooled. The separated solid is collected, washed with water, dried and recrystallized from ethanol to yield 3-chloro-6-methyl-5-(4-pyridinyl)-2(1H)-pyridinone.

Following the procedure described in Example F-1 or F-2 but using in place of 6-methyl-5-(4-pyridinyl)-2(1H)-pyridinone a molar equivalent quantity of the corresponding 1-$R_1$-6-(lower-alkyl)-5-PY-2(1H)-pyridinone and bromine or chlorine, it is contemplated that there can be obtained the 1-$R_1$-3-bromo(or chloro)-6(lower-alkyl)-5-PY-2(1H)-pyridinones of Examples F-3 through F-22.

F-3. 3-Chloro-6-ethyl-5-(4-pyridinyl)-2(1H)-pyridinone.
F-4. 3-Chloro-6-methyl-5-(3-pyridinyl)-2(1H)-pyridinone.
F-5. 3-Chloro-6-n-propyl-5-(4-pyridinyl)-2(1H)-pyridinone.
F-6. 3-Bromo-6-isopropyl-5-(4-pyridinyl)-2(1H)-pyridinone.
F-7. 3-Bromo-6-n-butyl-5-(4-pyridinyl)-2(1H)-pyridinone.
F-8. 3-Chloro-6-isobutyl-5-(4-pyridinyl)-2(1H)-pyridinone.
F-9. 3-Bromo-5-(4-pyridinyl)-6-tert.-butyl-2(1H)-pyridinone.
F-10. 3-Chloro-6-n-pentyl-5-(4-pyridinyl)-2(1H)-pyridinone.
F-11. 3-Bromo-6-ethyl-5-(2-methyl-4-pyridinyl)-2(1H)-pyridinone.
F-12. 3-Chloro-6-ethyl-5-(3-pyridinyl)-2(1H)-pyridinone.
F-13. 3-Chloro-1,6-dimethyl-5-(4-pyridinyl)-2(1H)-pyridinone.
F-14. 3-Chloro-6-ethyl-1-(2-hydroxyethyl)-5-(4-pyridinyl)-2(1H)-pyridinone.
F-15. 3-Chloro-6-methyl-5-(4-pyridinyl)-2(1H)-pyridinone.
F-16. 3-Bromo-1,6-diethyl-5-(4-pyridinyl)-2(1H)-pyridinone.
F-17. 3-Bromo-6-methyl-5-(2-pyridinyl)-2(1H)-pyridinone.
F-18. 3-Bromo-6-methyl-5-(5-methyl-2-pyridinyl)-2(1H)-pyridinone.
F-19. 3-Bromo-6-ethyl-5-(5-ethyl-2-pyridinyl)-2(1H)-pyridinone.
F-20. 3-Chloro-6-methyl-5-(4,6-dimethyl-2-pyridinyl)-2(1H)-pyridinone.
F-21. 3-Bromo-6-isopropyl-5-(6-methyl-2-pyridinyl)-2(1H)-pyridinone.
F-22. 3-Chloro-6-n-hexyl-5-(2-pyridinyl)-2(1H)-pyridinone.

G. 1-$R_1$-3-[MONO-or DI-(LOWER-ALKYL)AMINO]-5-PY-6-(LOWER-ALKYL)-2(1H)-PYRIDINONES

G-1. 6-Methyl-3-methylamino-5-(4-pyridinyl)-2(1H)-pyridinone, alternatively named 2-methyl-5- methylamino-[3,4'-bipyridin]-6(1H)-one —A mixture containing 19 g. of 3-bromo-6-methyl-5-(4-pyridinyl)-2(1H)-pyridinone, 250 cc. of 70% aqueous methylamine, 60 mg. of copper bronze and 60 mg. of cupric sulfate was autoclaved at 160° C. for forty-eight hours. The crystalline mass was taken up with warm aqueous methanol and the mixture filtered to collect the product. The solid (6 g.) plus another portion (1 g.) obtained by concentrating the mother liquor and diluting with methanol was dissolved in a small amount of acetic acid, filtered and the filtrate diluted with water. The resulting crystalline precipitate was collected, washed well with water and dried at 90° C. overnight to yield 5.1 g. of 6-methyl-3-methylamino-5-(4-pyridinyl)-2(1H)-pyridinone, m.p. 270°–275° C. with decomposition. This preparation also can be carried out as above using a molar equivalent quantity of 3-chloro-6-methyl-5-(4-pyridinyl)-2(1H)-pyridinone in place of 3-bromo-6-methyl-5-(4-pyridinyl)-2(1H)-pyridinone.

Acid-addition salts of 6-methyl-3-methylamino-5-(4-pyridinyl)-2(1H)-pyridinone are conveniently prepared by adding to a mixture of 5 g. of 6-methyl-3-methylamino-5-(4-pyridinyl)-2(1H)-pyridinone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 6-methyl-3-methylamino-5-(4-pyridinyl)-2(1H)-pyridinone and the appropriate acid, e.g., lactic acid or hydrochloric acid, to prepare respectively the monolactate or monohydrochloride salt in aqueous solution.

G-2. 3-Ethylamino-6-methyl-5-(4-pyridinyl)-2(1H)-pyridinone, alternatively named 5-ethylamino-2-methyl-[3,4'-bipyridin]-6(1H)-one, m.p. 250° C., 1.6 g., was prepared following the procedure described in Example G-1 but using 16.5 g. of 3-bromo-6-methyl-5-(4-pyridinyl)-2(1H)-pyridinone, 110 cc. of ethylamine, 15 cc. of water, 30 mg. of copper bronze, 30 mg. of cupric sulfate, autoclaving at 150° C. for forty-five hours and recrystallization twice from acetonitrile.

G-3. 6-Methyl-3-(dimethylamino)-5-(4-pyridinyl)-2(1H)-pyridinone, alternatively named 5-(dimethylamino)-2-methyl-[3,4'-bipyridin]-6(1H)-one—To a stirred solution containing 20 g. of 3-amino-6-methyl-5-(4-pyridinyl)-2(1H)-pyridinone dissolved in 200 cc. of formic acid was added dropwise with stirring over five minutes 20 cc. of 37% formaldehyde solution. The reaction mixture was refluxed for one hour and forty-five minutes, heated in vacuo to dryness and the residue taken up with methylene dichloride. The methylene dichloride solution was washed with saturated aqueous sodium bicarbonate solution and filtered. The filtrate was dried over anhydrous sodium sulfate, filtered and the solvent distilled off in vacuo to yield 14 g. of yellow crystalline solid. The solid was dissolved in 250 cc. of hot methylene dichloride, the hot solution treated with decolorizing charcoal and filtered, and the filtrate concentrated in vacuo to near dryness and then treated with acetonitrile. The resulting mixture of crystalline material and acetonitrile was cooled and the solid collected and dried to yield 10.5 g. of yellow crystalline product containing a trace impurity (shown by tlc). The solid was dissolved in chloroform solution and the trace impurity removed by filtering the chloroform solution through a 2 and ½ inch silica gel column. The resulting product (10.5 g.) was dissolved in methylene dichloride, the solution diluted with isopropyl alcohol and concentrated in vacuo, and chilled. The precipitate was collected and dried at 80° C. to yield 9.0 g. of 6-methyl-3(dimethylamino)-5-(4-pyridinyl)-2(1H)-pyridinone, m.p. 223°–225° C.

Following the procedure described in Example G-1 or G-2 but using in place of 3-bromo-6-methyl-5-(4-pyridinyl)-2(1H)-pyridinone a molar equivalent quantity of the appropriate 1-$R_1$-3-bromo (or chloro)-5-PY-6-(lower-alkyl)-2(1H)-pyridinone and the appropriate lower-alkylamine or di-(lower-alkyl)amine, it is contemplated that there can be obtained the 1-$R_1$-3-[mono- or di-(lower-alkyl)amino]-5-PY-6-(lower-alkyl)-2(1H)-pyridinones of Examples G-4 through G-23.

G-4. 6-Ethyl-3-methylamino-5-(4-pyridinyl)-2(1H)-pyridinone.

G-5. 3-Methylamino-6-methyl-5-(3-pyridinyl)-2(1H)-pyridinone.

G-6. 3-n-Propylamino-6-n-propyl-5-(4-pyridinyl)-2(1H)-pyridinone.

G-7. 3-Methylamino-6-isopropyl-5-(4-pyridinyl)-2(1H)-pyridinone.

G-8. 6-n-Butyl-3-dimethylamino-5-(4-pyridinyl)-2(1H)-pyridinone.

G-9. 3-n-Butylamino-6-isobutyl-5-(4-pyridinyl)-2(1H)-pyridinone.

G-10. 3-Methylamino-5-(4-pyridinyl)-6-tert.-butyl-2(1H)-pyridinone.

G-11. 3-Isopropylamino-6-n-pentyl-5-(4-pyridinyl)-2(1H)-pyridinone.

G-12. 6-Ethyl-3-diethylamino-5-(2-methyl-4-pyridinyl)-2(1H)-pyridinone.

G-13. 6-Ethyl-3-ethylamino-5-(3-pyridinyl)-2(1H)-pyridinone.

G-14. 3-Methylamino-1,6-dimethyl-5-(4-pyridinyl)-2(1H)-pyridinone.

G-15. 6-Ethyl-3-ethylamino-1-(2-hydroxyethyl)-5-(4-pyridinyl)-2(1H)-pyridinone.

G-16. 1-Ethyl-6-methyl-3-methylamino-5-(4-pyridinyl)-2(1H)-pyridinone.

G-17. 1,6-Diethyl-3-methylamino-5-(4-pyridinyl)-2(1H)-pyridinone.

G-18. 3-n-Hexylamino-6-methyl-5-(2-pyridinyl)-2(1H)-pyridinone.

G-19. 3-Ethylamino-6-methyl-5-(5-methyl-2-pyridinyl)-2(1H)-pyridinone.

G-20. 6-Ethyl-5-(5-ethyl-2-pyridinyl)-3-dimethylamino-2(1H)-pyridinone.

G-21. 3-Diisopropylamino-6-methyl-5-(4,6-dimethyl-2-pyridinyl)-2(1H)-pyridinone.

G-22. 3-Ethylamino-6-isopropyl-5-(6-methyl-2-pyridinyl)-2(1H)-pyridinone.

G-23. 3-Methylamino-6-n-hexyl-5-(2-pyridinyl)-2(1H)-pyridinone.

H.
1-$R_1$-3-(LOWER-ACYLAMINO)-6-(LOWER-ALKYL)-5-PY-2(1H)-PYRIDINONES

H-1. 3-Acetylamino-6-methyl-5-(4-pyridinyl)-2(1H)-pyridinone, alternatively named N-[1,2-dihydro-6-methyl-2-oxo-5-(4-pyridinyl)]acetamide—A mixture containing 10.1 g. of 3-amino-6-methyl-5-(4-pyridinyl)-2(1H)-pyridinones, 5.7 g. of acetic anhydride and 120 ml. of pyridine is heated on a steam bath for one hour and then allowed to cool. The separated product is collected washed with ether, dried and recrystallized from dimethylformamide to produce 3-acetylamino-6-methyl-5-(4-pyridinyl)-2(1H)-pyridinone.

Acid-addition salts of 3-acetylamino-6-methyl-5-(4-pyridinyl)-2(1H)-pyridinone are conveniently prepared by adding to a mixture of 5 g. of 3-acetylamino-6-methyl-5-(4-pyridinyl)-2(1H)-pyridinone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 3-acetylamino-6-methyl-5-(4-pyridinyl)-2(1H)-pyridinone and the appropriate acid, e.g., lactic acid or hydrochloric acid, to prepare respectively the monolactate or monohydrochloride salt in aqueous solution.

H-2. 3-[2-(Acetoxy)propanoylamino]-6-methyl-2(1H)-pyridinone—To a stirred mixture containing 20.1 g. of 3-amino-6-methyl-5-(4-pyridinyl)-2(1H)-pyridinone and 300 ml. of pyridine at room temperature is added dropwise over a period of about one hour 16.5 g. of 2-acetoxypropanoyl chloride and the resulting mixture is cooled in an ice bath. The product that separates is collected, washed with ether, dried, recrystallized from methanol, washed successively with ethanol and ether and dried to produce 3-[2-(acetoxy)-propanoylamino]-6-methyl-2(2H)-pyridinone.

Following the procedure described in Example H-1 or H-2 but using in place of 3-amino-6-methyl-5-(4-pyridinyl)-2(1H)-pyridinone and/or acetic anhydride or 2-acetoxypropanoyl chloride molar equivalent quantities of the corresponding 1-$R_1$-3-amino-5-PY-6-(lower-alkyl)-2(1H)-pyridinone and/or appropriate lower-acrylating agents, it is contemplated that there can be obtained the 3-(lower-acylamino)-5-PY-6-(lower-alkyl)-2(1H)-pyridinones of Examples H-3 through H-17.

H-3. 3-Acetylamino-6-ethyl-5-(4-pyridinyl)-2(1H)-pyridinone.

H-4. 6-Methyl-3-propionylamino-5-(3-pyridinyl)-2(1H)-pyridinone.

H-5. 3-Butyrylamino-6-n-propyl-5-(4-pyridinyl)-2(1H)-pyridinone.

H-6. 6-n-Butyl-3-acetylamino-5-(4-pyridinyl)-2(1H)-pyridinone.

H-7. 3-Formylamino-6-isobutyl-2-oxo-5-(4-pyridinyl)-2-(1H)-pyridinyl.

H-8. 3-Acetylamino-6n-pentyl-5-(4-pyridinyl)-2(1H)pyridinone.

H-9. 3-[2-(Acetoxy)propanoylamino]-6-ethyl-5-(2-methyl-4-pyridinyl)-2(1H)-pyridinone.

H-10. 6-Ethyl-3-propionylamino-5-(3-pyridinyl)-2(1H)-pyridinone.

H-11. 3-Acetylamino-1,6-dimethyl-2-oxo-5-(4-pyridinyl)-2(1H)-pyridinone.

H-12. 3-Acetyl-6-ethyl-1-(2-hydroxyethyl)-5-(4-pyridinyl)-2(1H)-pyridinone.

H-13. 1,6-Diethyl-3-propionylamino-5-(4-pyridinyl)-2(1H)-pyridinone.

H-14. 3-Acetylamino-6-methyl-5-(2-pyridinyl)-2(1H)-pyridinone.

H-15. 6-Ethyl-5-(5-ethyl-2-pyridinyl)-3-formylamino-2(1H)-pyridinone.

H-16. 3-Acetylamino-6-methyl-5-(4,6-dimethyl-2-pyridinyl)-2(1H)-pyridinone.

H-17. 3-Acetylamino-6-n-hexyl-5-(2-pyridinyl)-2(1H)-pyridinone.

The usefulness of the compounds of formula I or salt thereof, as cardiotonic agents is demonstrated by their effectiveness in standard pharmacological test procedures, for example, in causing a significant increase in contractile force in the Isolated Cat Atria and Papillary Muscle Procedure and in causing a significant increase in cardiac contractile force in the Anesthetized Dog Procedure with low or minimal changes in heart rate and blood pressure. Detailed descriptions of these test procedures appear in U.S. Pat. No. 4,072,746, issued Feb. 7, 1980.

When tested by the above-noted Isolated Cat Atria and Papillary Muscle Procedure, the compounds of formula I when tested at doses of 3, 10 or 30 μg./ml., were found to cause a significant increase, that is, greater than 25%, in papillary muscle force and a significant increase, that is, greater than 25%, in right atrial force, while causing only a low percentage increase (about one-third or less than the percentage increase in right atrial force or papillary muscle force) in right atrial rate. Moreover, the 6-(lower-alkyl) compounds of formula I unexpectedly were found to be markedly more active as cardiotonics when tested by this procedure in comparison with the corresponding prior art 6-des-(lower-alkyl) compounds. Also, some of them, e.g., those where Q in formula I is carbamyl and bromo, were found to be active as cardiotonics whereas, in contrast, the corresponding 6-des-(lower-alkyl) compounds are shown only as intermediates, not as having cardiotonic properties.

The markedly higher cardiotonic activity of the 6-(lower-alkyl) compounds over the corresponding prior art 6-unsubstituted compounds is illustrated by the following comparisons of test data obtained using said isolated cat atria and papillary muscle procedure: the percentage increases in papillary muscle force and right atrial force for 3-amino-6-methyl-5-(4-pyridinyl)-2(1H)-pyridinone were found to be 96% and 74% when tested at 10 μg/ml. compared with corresponding increases of 109±11.3% and 49.9±8.4% for 3-amino-5-(4-pyridinyl)-2(1H)-pyridinone (amrinone) tested at 100 μg./ml., that is, ten times the dose; the percentage increases in papillary muscle force and right atrial force for 3-amino-6-ethyl-5-(4-pyridinyl)-2(1H)-pyridine were found to be 53% and 37% when tested at 3 μg./ml. compared with corresponding increases of 54.1±5.3% and 33.6±4.4% for 3-amino-5-(4-pyridinyl)-2(1H)-pyridinone tested at 30 μg./ml., that is, ten times the dose; the percentage increases in papillary muscle force and right atrial force for 1,2-dihydro-6-methyl-2-oxo-5-(4-pyridinyl)nicotinonitrile and 6-ethyl-1,2-dihydro-2-oxo-5-(4-pyridinyl)nicotinonitrile were found to be 45% and 51% for the 6-methyl compound and 107% and 79% for the 6-ethyl compound when tested at 3 μg./ml. compared with corresponding increases of 65% and 15% for prior art 6-desalkyl 1,2-dihydro-2-oxo-5-(4-pyridinyl)nicotinonitrile at 30 μg./ml., that is, ten times the dose; the percentage increases in papillary muscle force and right atrial force for 1,2-dihydro-6-methyl-2-oxo-5-(4-pyridinyl)-nicotinonitrile were found to be 135% and 102% when tested at 10 μg./ml. whereas the corresponding 6-desmethyl prior art compound was inactive at 10 μg./ml.; the percentage increases in papillary muscle force and right atrial force for 6-methyl-3-methylamino-5-(4-pyridinyl)-2(1H)-pyridinone were found to be 68% and 41% when tested at 30 μg./ml. compared with corresponding increases of 64% and 39% for prior art 3-methylamino-5-(4-pyridinyl)-2(1H)-pyridinone when tested at 100 μg./ml., that is, over three times the dose.

Illustrative of cardiotonically-active compounds of formula I where Q is carbamyl and halo whereas the corresponding prior art 6-des-(lower-alkyl) compounds are shown only as intermediates and not as cardiotonic agents are: 1,2-dihydro-6-methyl-2-oxo-5-(4-pyridinyl)-nicotinamide when tested by the in vitro cat atria and papillary muscle test was found to show percentage increases in papillary muscle force and right atrial force of 35% and 22% respectively at 30 μg./ml. and 87% and 37% respectively at 100 μg./ml.; 6-ethyl-1,2-dihydro-2-oxo-5-(4-pyridinyl)nicotinamide when tested by the same method was found to show percentage increases in papillary muscle force and right atrial force of 29% and 7% respectively at 100 μg./ml. and 89 and 29% respectively at 300 μg./ml.; and, 3-bromo-6-methyl-5-(4-pyridinyl)-2(1H)-pyridinone when tested by said in vitro cat atria and papillary muscle test was found to show percentage increases in papillary muscle force and right atrial force of 87% and 99% respectively at 1.0 μg./ml. and 107% and 58% respectively at 10 μg./ml.

When tested by the above-noted Anesthetized Dog Procedure, compounds of formula I when administered intravenously as a single bolus injection of 0.01, 0.03, 0.10, 0.30, 1.0 and/or 3.0 mg./kg. caused a significant increase, that is, greater than 25%, in cardiac contractile force or cardiac contractility with only low or minimal changes (less than 25%) in heart rate and blood pressure. Moreover, the 6-(lower-alkyl) compounds of formula I I were found to be markedly more active as cardiotonics when tested by this procedure in comparison with the corresponding prior art 6-des-(lower-alkyl) compounds, as evidenced by the following illustrations: the percentage increase on the cardiac contractile force or cardiac contractility for 3-amino-6-methyl-5-(4-pyridinyl)-2(1H)-pyridinone when tested as indicated in the anesthetized dog at 1.0 mg./kg. intravenously was found to be 136% compared with 125.67±10.59% for the corresponding 6-desmethyl compound, amrinone, when tested at ten times the dose, that is, at 10 mg./kg. intravenously; similarly, the percentage increases in cardiac contractile force for 3-amino-6-ethyl-5-(4-pyridinyl)-2(1H)-pyridinone when tested by the same procedure at 0.03 mg./kg. and 0.10 mg./kg. iv. were found to be 33% and 72% respectively compared with 24.67±3.15% and 70.63±7.85% respectively for prior art amrinone when tested at ten times the respective doses, that is, at 0.3 mg./kg. and 1.0 mg./kg. iv.; the percentage increases in cardiac contractility for 1,2-dihydro-6-methyl-2-oxo-5-(4-pyridinyl)nicotinonitrile when tested by the same procedure at 0.03 mg./kg. and 0.10 mg./kg. were found to be 49.5% and 87.5% respectively compared with 44% and 78% respectively for the corresponding prior art 6-desmethyl compound when tested at one hundred times the respective doses, that is, at 3 mg./kg. and 10 mg./kg. or compared with 24.67±3.15% and 70.63±7.85% respectively for the prior art amrinone when tested at ten times the respective doses, that is, at 0.3 mg./kg. and 1.0 mg./kg. respectively; similarly, the percentage increases in contractile force for 6-ethyl-1,2-dihydro-2-oxo-5-(4-pyridinyl)-nicotinonitrile when tested by this procedure at doses of 0.03 mg./kg. and 0.10 mg./kg. were found to be 68.5% and 135% respectively compared witth 44% and 78% respectively for the corresponding prior art 6-desmethyl compound when tested at one hundred times the respective dose levels, that is, at 3 mg./kg. and 10 mg./kg. respectively.

The present invention includes within its scope a cardiotonic composition for increasing cardiac contractility, said composition comprising a pharmaceutically-acceptable carrier and, as the active component thereof, the cardiotonic 1-$R_1$-3-Q-6-(lower-alkyl)-5-PY-2(1H)-pyridinone of formula I or pharmaceutically-acceptable acid-addition or cationic salt thereof. The invention also includes within its scope the method for increasing cardiac contractility in a patient requiring such treatment which comprises administering to such patient an effective amount of said 1-$R_1$-3-Q-6-(lower-alkyl)-5-PY-2(1H)-pyridinone of formula I or pharmaceutically-acceptable acid-addition or cationic salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavouring, perfuming and preserving agents. According to the invention, the compounds for oral administration also include capsules for absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, preserving, wetting, emulsifying and dispersing agents.

They may be sterilized, for example by filtration through a bacteria-retaining filter, by incorporation of sterilising agents in the compositions, by irradiation or by heating. They may also be manufactured in the form of sterile solid compositions which can be dissolved in sterile water or some other sterile injectable medium immediately before use.

The percentages of active components in the said composition and method for increasing cardiac contractility may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. A 1-$R_1$-3-Q-5-PY-6-R-2(1H)-pyridinone having the formula

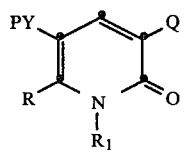

where Q is amino, cyano, carbamyl, halo, lower-alkylamino, di-(lower-alkyl)amino or lower-acylamino, $R_1$ is hydrogen, lower-alkyl or lower-hydroxyalkyl, R is lower-alkyl and PY is 4-, 3- or 2-pyridinyl or 4-, 3- or 2-pyridinyl having one or two lower-alkyl substituents, or pharmaceutically-acceptable acid-addition or cationic salt thereof.

2. A compound according to claim 1 where Q is amino.

3. A compound according to claim 1 where Q is cyano.

4. A compound according to claim 1 where Q is carbamyl.

5. A compound according to claim 1 where Q is halo.

6. A compound according to claim 1 where Q is lower-alkylamino.

7. A compound according to claim 1 where Q is di-(lower-alkyl)amino.

8. A compound according to claim 1 where Q is lower-acylamino.

9. 3-Amino-6-methyl-5-(4-pyridinyl)-2(1H)-pyridinone or pharmaceutically-acceptable acid-addition salt thereof.

10. 3-Amino-6-ethyl-5-(4-pyridinyl)-2(1H)-pyridinone or pharmaceutically-acceptable acid-addition salt thereof.

11. 3-Amino-6-n-propyl-5-(4-pyridinyl)-2(1H)-pyridinone or pharmaceutically-acceptable acid-addition salt thereof.

12. 1,2-Dihydro-6-methyl-2-oxo-5-(4-pyridinyl)-nicotinonitrile or pharmaceutically-acceptable acid-addition salt thereof.

13. 6-Methyl-3-methylamino-5-(4-pyridinyl)-2(1H)-pyridinone or pharmaceutically-acceptable acid-addition salt thereof.

14. 3-Bromo-6-methyl-5-(4-pyridinyl)-2(1H)-pyridinone or pharmaceutically-acceptable acid-addition salt thereof.

15. 6-Ethyl-1,2-dihydro-2-oxo-5-(4-pyridinyl)-nicotinonitrile according to claim 3.

16. 1,2-Dihydro-6-methyl-2-oxo-5-(4-pyridinyl)-nicotinamide according to claim 4.

17. 6-Ethyl-1,2-dihydro-2-oxo-5-(4-pyridinyl)-nicotinamide according to claim 4.

18. 3-Ethylamino-6-methyl-5-(4-pyridinyl)-2(1H)-pyridinone according to claim 6.

19. 3-Dimethylamino-6-methyl-5-(4-pyridinyl)-2(1H)-pyridinone according to claim 7.

20. A cardiotonic composition for increasing cardiac contractility, said composition comprising a pharmaceutically-acceptable inert carrier and, as the active component thereof, an effective amount of a cardiotonic 1-$R_1$-3-Q-5-PY-6-R-2(1H)pyridinone having the formula

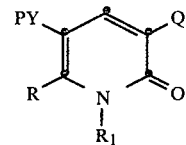

where Q is amino, cyano, carbamyl, halo, lower-alkylamino, di-(lower-alkyl)amino or lower-acylamino, $R_1$ is hydrogen, lower-alkyl or lower-hydroxyalkyl, R is lower-alkyl and PY is 4-, 3- or 2-pyridinyl or 4-, 3- or 2-pyridinyl having one or two lower-alkyl substituents, or pharmaceutically-acceptable acid-addition or cationic salt thereof.

21. A composition according to claim 20 where the active component is 3-amino-6-methyl-5-(4-pyridinyl)-2(1H)-pyridinone or pharmaceutically-acceptable acid-addition salt thereof.

22. A composition according to claim 20 where the active component is 1,2-dihydro-6-methyl-2-oxo-5-(4-pyridinyl)nicotinonitrile or pharmaceutically-acceptable acid-addition salt thereof.

23. A composition according to claim 20 where the active component is 3-amino-6-ethyl-5-(4-pyridinyl)-2(1H)-pyridinone or pharmaceutically-acceptable acid-addition salt thereof.

24. The method for increasing cardiac contractility in a patient requiring such treatment which comprises administering orally or parenterally in a solid or liquid dosage form to such patient an effective amount of a cardiotonic 1-$R_1$-3-Q-5-PY-6-R-2(1H)-pyridinone having the formula

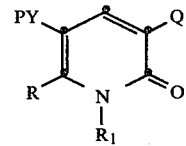

where Q is amino, cyano, carbamyl, halo, lower-alkylamino, di-(lower-alkyl)amino or lower-acylamino, $R_1$ is hydrogen, lower-alkyl or lower-hydroxyalkyl, R is lower-alkyl and PY is 4-, 3- or 2-pyridinyl or 4-, 3- or 2-pyridinyl having one or two lower-alkyl substituents, or pharmaceutically-acceptable acid-addition or cationic salt thereof.

25. The method according to claim 24 where Q is amino, R is methyl or ethyl, and PY is 4-pyridinyl.

26. The method according to claim 24 where Q is cyano, R is methyl or ethyl, and PY is 4-pyridinyl.

* * * * *

UNITED STATES PATENT AND TRADEMARK OFFICE
CERTIFICATE OF CORRECTION

PATENT NO. : 4,313,951
DATED : February 2, 1982
INVENTOR(S) : George Y. Lesher et al.

It is certified that error appears in the above–identified patent and that said Letters Patent are hereby corrected as shown below:

Column 26, line 36, "capsules for" should read -- capsules of --.

Signed and Sealed this

Fourteenth Day of December 1982

[SEAL]

Attest:

GERALD J. MOSSINGHOFF

Attesting Officer    Commissioner of Patents and Trademarks

UNITED STATES PATENT AND TRADEMARK OFFICE

CERTIFICATE EXTENDING PATENT TERM
UNDER 35 U.S.C. 156

Patent No.    : 4,313,951

Dated         : February 2, 1982

Inventor(s)   : George Y. Lesher et al

Patent Owner  : Sterling Drug Inc.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this Twenty-Eighth day of December 1988.

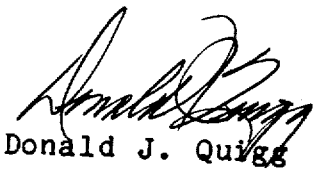

Donald J. Quigg

Assistant Secretary and Commissioner of Patents and Trademarks